(12) United States Patent
Wendlinger et al.

(10) Patent No.: US 11,084,768 B2
(45) Date of Patent: Aug. 10, 2021

(54) PROCESS FOR THE PRODUCTION OF 2,3,3,3-TETRAFLUOROPROPENE

(71) Applicant: Arkema France, Colombes (FR)

(72) Inventors: Laurent Wendlinger, Pierre-Benite (FR); Dominique Deur-Bert, Pierre-Benite (FR); Anne Pigamo, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/976,599

(22) PCT Filed: Mar. 4, 2019

(86) PCT No.: PCT/FR2019/050479
§ 371 (c)(1),
(2) Date: Aug. 28, 2020

(87) PCT Pub. No.: WO2019/170991
PCT Pub. Date: Sep. 12, 2019

(65) Prior Publication Data
US 2021/0002188 A1 Jan. 7, 2021

(30) Foreign Application Priority Data
Mar. 7, 2018 (FR) ...................... 1851954

(51) Int. Cl.
*C07C 17/20* (2006.01)
*C07C 17/25* (2006.01)
*C07C 21/18* (2006.01)
*B01J 23/26* (2006.01)

(52) U.S. Cl.
CPC ............. *C07C 17/204* (2013.01); *B01J 23/26* (2013.01); *C07C 17/20* (2013.01); *C07C 17/206* (2013.01); *C07C 17/25* (2013.01); *C07C 21/18* (2013.01)

(58) Field of Classification Search
CPC ............................. C07C 17/206; C07C 17/25
See application file for complete search history.

(56) References Cited

U.S. PATENT DOCUMENTS

| | | | |
|---|---|---|---|
| 2,773,014 A | 12/1956 | Snuggs et al. | |
| 4,902,838 A | 2/1990 | Manzer et al. | |
| 5,227,350 A | 7/1993 | Scott et al. | |
| 5,322,597 A | 6/1994 | Childs et al. | |
| 5,334,784 A | 8/1994 | Blake et al. | |
| 5,919,728 A | 7/1999 | Rinaldi et al. | |
| 8,614,361 B2 | 12/2013 | Suzuki et al. | |
| 8,618,338 B2 | 12/2013 | Elsheikh et al. | |
| 9,255,045 B2 | 2/2016 | Pigamo et al. | |
| 9,340,473 B2 | 5/2016 | Pigamo et al. | |
| 9,708,234 B2 | 7/2017 | Chaki et al. | |
| 9,834,499 B2 | 12/2017 | Pigamo et al. | |
| 10,227,275 B2 | 3/2019 | Pigamo et al. | |
| 10,427,998 B2 | 10/2019 | Pigamo et al. | |
| 10,532,965 B2 | 1/2020 | Pigamo et al. | |
| 2009/0240054 A1 | 9/2009 | Merkel et al. | |
| 2009/0287026 A1 | 11/2009 | Kopkalli et al. | |
| 2010/0191025 A1 | 7/2010 | Perdrieux | |
| 2011/0031436 A1 | 2/2011 | Mahler et al. | |
| 2013/0197281 A1 | 8/2013 | Hintzer et al. | |
| 2013/0267740 A1 | 10/2013 | Wendlinger et al. | |
| 2014/0012051 A1 | 1/2014 | Pigamo et al. | |
| 2014/0039228 A1 | 2/2014 | Pigamo et al. | |
| 2014/0275653 A1 | 9/2014 | Pigamo et al. | |
| 2015/0008357 A1 | 1/2015 | Furuta et al. | |
| 2015/0197467 A1 | 7/2015 | Pigamo et al. | |

(Continued)

FOREIGN PATENT DOCUMENTS

| | | |
|---|---|---|
| CN | 107540011 A | 1/2018 |
| EP | 0 449 617 A2 | 10/1991 |

(Continued)

OTHER PUBLICATIONS

International Search Report (PCT/ISA/210) and translation and Written Opinion (PCT/ISA/237) dated Jun. 26, 2019, by the European Patent Office as the International Searching Authority for International Application No. PCT/FR2019/050478.
International Search Report (PCT/ISA/210) dated Jun. 19, 2019, by the European Patent Office as the International Searching Authority for International Application No. PCT/FR2019/050477.
Written Opinion (PCT/ISA/237) dated Jun. 19, 2019, by the European Patent Office as the International Searching Authority for International Application No. PCT/FR2019/050477.
Mukerjee, et al., "Effect of temperature on the electrical conductivity and the thermodynamics of micelle formation of sodium perfluorooctanoate", Journal of Physical Chemistry, vol. 89, No. 21, Nov. 1, 1985, pp. 5308-5312.
Bonnet, "Liquid-phase HF Fluorination", Multiphase Homogeneous Catalysis, 5.2 State of the Art, 2002 (month unknown), pp. 535-542.

(Continued)

*Primary Examiner* — Medhanit W Bahta
(74) *Attorney, Agent, or Firm* — Buchanan Ingersoll & Rooney P.C.

(57) ABSTRACT

A process for the production of 2,3,3,3-tetrafluoropropene including the stages: i) in a first reactor, bringing a stream A including 2-chloro-3,3,3-trifluoropropene into contact with hydrofluoric acid in the gas phase in the presence of a catalyst in order to produce a stream B including 2,3,3,3-tetrafluoropropene, HCl, HF and unreacted 2-chloro-3,3,3-trifluoropropene; and ii) in a second reactor, bringing hydrofluoric acid into contact, in the gas phase in the presence or not of a catalyst, with a stream including at least one chlorinated compound selected from the group of 1,1,1,2,3-pentachloropropane, 2,3-dichloro-1,1,1-trifluoropropane, 2,3,3,3-tetrachloropropene and 1,1,2,3-tetrachloropropene, in order to produce a stream C including 2-chloro-3,3,3-trifluoropropene, wherein the stream B obtained in stage i) feeds the second reactor used for stage ii); and wherein the electrical conductivity of the stream A provided in stage i) is less than 15 mS/cm.

13 Claims, No Drawings

(56) References Cited

U.S. PATENT DOCUMENTS

| | | | |
|---|---|---|---|
| 2015/0203422 A1* | 7/2015 | Deur-Bert | C07C 17/383 570/156 |
| 2016/0115104 A1 | 4/2016 | Pigamo et al. | |
| 2016/0237009 A1 | 8/2016 | Deur-bert et al. | |
| 2017/0158586 A1 | 6/2017 | Collier et al. | |
| 2017/0210686 A1 | 7/2017 | Pigamo et al. | |
| 2018/0093934 A1 | 4/2018 | Pigamo et al. | |
| 2018/0148394 A1 | 5/2018 | Pigamo et al. | |
| 2019/0127303 A1 | 5/2019 | Ondrus et al. | |
| 2019/0152883 A1 | 5/2019 | Pigamo et al. | |
| 2019/0375698 A1 | 12/2019 | Pigamo et al. | |
| 2020/0407293 A1 | 12/2020 | Wendlinger et al. | |
| 2021/0002189 A1 | 1/2021 | Wendlinger et al. | |

FOREIGN PATENT DOCUMENTS

| | | | |
|---|---|---|---|
| EP | 0582192 A1 | 2/1994 | |
| EP | 0 939 071 A1 | 9/1999 | |
| FR | 3 013 606 | 5/2015 | |
| WO | 0181353 A1 | 11/2001 | |
| WO | 2007079431 A2 | 7/2007 | |
| WO | WO 2008/040969 A2 | 4/2008 | |
| WO | WO 2008/054781 A1 | 5/2008 | |
| WO | 2008149011 A2 | 12/2008 | |
| WO | WO 2009/118628 A1 | 10/2009 | |
| WO | 2009137658 A2 | 11/2009 | |
| WO | 2011077192 A1 | 6/2011 | |
| WO | 2012012113 A1 | 1/2012 | |
| WO | 2012052797 A1 | 4/2012 | |
| WO | WO 2012/098421 A1 | 7/2012 | |
| WO | WO 2012/098422 A1 | 7/2012 | |
| WO | 2013088195 A1 | 6/2013 | |
| WO | WO 2013/154059 A1 | 10/2013 | |
| WO | WO 2013/182816 A1 | 12/2013 | |
| WO | WO 2014/010750 A1 | 1/2014 | |
| WO | 2017178857 A1 | 10/2017 | |

OTHER PUBLICATIONS

International Search Report (PCT/ISA/210) dated Jun. 6, 2019, by the French Patent Office as the International Searching Authority for International Application No. PCT/FR2019/050479.
Written Opinion (PCT/ISA/237) dated Jun. 6, 2019, by the French Patent Office as the International Searching Authority for International Application No. PCT/FR2019/050479.
U.S. Appl. No. 16/250,141, Anne Pigamo, Laurent Wendlinger, Dominque Duer-Bert, filed Jan. 17, 2019, (Cited herein as US Patent Application Publication No. 2019/0152883 A1 of May 2, 2019).
U.S. Appl. No. 16/545,294, Anne Pigamo and Bertrand Collier, filed Aug. 20, 2019 (Cited herein as US Patent Application Publication No. 2019/0375698 A1 of Dec. 12, 2019).
U.S. Appl. No. 17/053,250, Anne Pigamo and Cédric Lavy, filed Nov. 5, 2020.
U.S. Appl. No. 17/053,250, filed Nov. 5, 2020, Pigamo et al.
International Search Report (PCT/ISA/210) and Written Opinion (PCT/ISA/237), issued in PCT/FR2015/051653, dated Sep. 1, 2015, European Patent Office, Rijswijk, NL, 19 pages.
Wendlinger, Laurent, et al., U.S. Appl. No. 16/976,819, entitled "Process for the Production of 2,3,3,3-Tetrafluoropropene," filed Aug. 31, 2020.
Wendlinger, Laurent, et al., U.S. Appl. No. 16/976,520, entitled "Process for Producing 2-Chloro-3,3,3-Trifluoropropene," filed Aug. 28, 2020.
Pigamo, Anne, et al., U.S. Appl. No. 17/053,250 entitled "Method for Producing 1-Chloro-3,3,3-Trifluoropropene," filed Nov. 5, 2020.
U.S. Appl. No. 17/251,328, Kevin Hisler, Anne Pigamo, Laurent Wendlinger and Emmanuel Boussarie, filed Dec. 11, 2020.
U.S. Appl. No. 17/251,328, filed Dec. 11, 2020, Hisler et al.
Hisler, Kevin, et al., U.S. Appl. No. 17/251,328, entitled "Method for Producing 1-Chloro-3,3,3-Trifluoropropene," filed Dec. 11, 2020.
U.S. Appl. No. 17/280,547, dated Mar. 26, 2021, Boutier et al.
**Boutier, Jean-Christophe, et al., et al., U.S. Appl. No. 17/280,547, entitled "Stabilization of 1-Chloro-3,3,3-Trifluoropropene," filed in the U.S. Patent and Trademark Office dated Mar. 26, 2021.

* cited by examiner

PROCESS FOR THE PRODUCTION OF 2,3,3,3-TETRAFLUOROPROPENE

TECHNICAL FIELD OF THE INVENTION

The present invention relates to the production of hydrofluoroolefins. More particularly, the present invention relates to the production of 2,3,3,3-tetrafluoropropene.

TECHNOLOGICAL BACKGROUND OF THE INVENTION

Halogenated hydrocarbons, in particular fluorinated hydrocarbons, such as hydrofluoroolefins, are compounds which have a structure of use as functional materials, solvents, refrigerants, inflation agents and monomers for functional polymers or starting materials for such monomers. Hydrofluoroolefins, such as 2,3,3,3-tetrafluoropropene (HFO-1234yf), are attracting attention because they offer a promising behavior as refrigerants having a low global warming potential.

Processes for the production of fluoroolefins are usually carried out in the presence of a starting substance, such as a chlorine-containing alkane or a chlorine-containing alkene, and in the presence of a fluorinating agent, such as hydrogen fluoride. These processes can be carried out in the gas phase or in the liquid phase, in the absence or not of a catalyst.

For example, US 2009/0240090 discloses a gas-phase process for the preparation of 2-chloro-3,3,3-trifluoropropene (HCFO-1233xf) from 1,1,1,2,3-pentachloropropane (HCC-240db). The HCFO-1233xf thus produced is converted into 2-chloro-1,1,1,2-tetrafluoropropane (HCFC-244bb) in the liquid phase and then the latter is converted into 2,3,3,3-tetrafluoropropene.

WO 2011/077192 also discloses a process for the preparation of 2,3,3,3-tetrafluoropropene comprising in particular a stage in which 2-chloro-3,3,3-trifluoropropene is brought into contact with HF in the gas phase in the presence of a fluorination catalyst.

There is still a need for more effective processes for the production of 2,3,3,3-tetrafluoropropene.

SUMMARY OF THE INVENTION

The present invention relates to a process for the production of 2,3,3,3-tetrafluoropropene comprising the stages:

i) in a first reactor, bringing a stream A comprising 2-chloro-3,3,3-trifluoropropene into contact with hydrofluoric acid in the gas phase in the presence of a catalyst in order to produce a stream B comprising 2,3,3,3-tetrafluoropropene, HCl, HF and unreacted 2-chloro-3,3,3-trifluoropropene; and ii) in a second reactor, bringing hydrofluoric acid into contact, in the gas phase in the presence or not of a catalyst, with a stream comprising at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream C comprising 2-chloro-3,3,3-trifluoropropene, characterized in that the stream B obtained in stage i) feeds said second reactor used for stage ii); and in that the electrical conductivity of said stream A provided in stage i) is less than 15 mS/cm.

The present process makes it possible to optimize and improve the production of 2,3,3,3-tetrafluoropropene. An electrical conductivity value of less than 15 mS/cm of the stream A before the implementation of the fluorination or dehydrohalogenation stage makes it possible to guarantee an optimal effectiveness of the reaction in terms of conversion and of selectivity. If a catalyst is present, such a value makes it possible to also guarantee an optimal effectiveness of the catalyst.

According to a preferred embodiment, stage i) is carried out in the presence of a catalyst, preferably a chromium-based catalyst; in particular, said catalyst comprises a chromium oxyfluoride or a chromium oxide or a chromium fluoride or a mixture of these; and stage ii) is carried out in the presence or in the absence of a catalyst; advantageously, stage ii) is carried out in the presence of a catalyst, preferably a chromium-based catalyst; in particular, said catalyst comprises a chromium oxyfluoride or a chromium oxide or a chromium fluoride or a mixture of these.

According to a preferred embodiment, the catalyst is based on chromium and also comprises a cocatalyst selected from the group consisting of Ni, Zn, Co, Mn and Mg; preferably, the content of cocatalyst is between 0.01% and 10%, based on the total weight of the catalyst.

According to a preferred embodiment, the stream C also comprises 2,3,3,3-tetrafluoropropene, HF, HCl and 1,1,1,2,2-pentafluoropropane.

According to a preferred embodiment, the stream C is purified, preferably by distillation, in order to form a stream C1 comprising 2,3,3,3-tetrafluoropropene, HCl and 1,1,1,2,2-pentafluoropropane, and a stream C2 comprising HF and 2-chloro-3,3,3-trifluoropropene.

According to a preferred embodiment, said stream C2 is recycled in stage i).

According to a preferred embodiment, said stream C2 recycled in stage i) has an electrical conductivity of less than 15 mS/cm.

According to a preferred embodiment, said stream B and said at least one chlorinated compound are brought into contact prior to the entry of these into said second reactor.

According to a preferred embodiment, the pressure at the inlet of said first reactor of stage i) is greater than the pressure at the inlet of said second reactor of stage ii); preferably, the pressure difference between the pressure at the inlet of said first reactor and the pressure at the inlet of said second reactor is from 100 mbar to 3.5 bar, advantageously from 150 mbar to 3.0 bar, preferably from 300 mbar to 2.5 bar, more preferentially from 400 mbar to 2.0 bar, in particular from 750 mbar to 1.75 bar, more particularly from 1 to 1.5 bar.

According to a preferred embodiment, the temperature at which stage i) is carried out is different from that at which stage ii) is carried out; and the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C.; and less than 60° C., advantageously less than 55° C., preferably less than 50° C., more preferentially less than 45° C., in particular less than 40° C., more particularly less than 35° C., favorably less than 30° C., preferentially favorably less than 25° C., particularly favorably less than 20° C.

According to a preferred embodiment, stage i) is carried out at a temperature which is lower than the temperature at which stage ii) is carried out; and the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C.; and less than 60° C., advantageously less than 55° C., preferably less than 50° C., more preferentially less than 45° C., in particular less than 40° C., more particularly less than 35° C., favorably less than 30° C., preferentially favorably less than 25° C., particularly favorably less than 20° C.

According to a preferred embodiment, the stream C is cooled to a temperature of less than 100° C., then distilled in order to form a stream C1 comprising 2,3,3,3-tetrafluoropropene, HCl and 1,1,1,2,2-pentafluoropropane, and a stream C2 comprising HF and 2-chloro-3,3,3-trifluoropropene; the temperature at the distillation column top is from −35° C. to 10° C. and the distillation is carried out at a pressure from 2 to 6 bara; said second stream obtained at the distillation column bottom is recycled in stage i).

According to a preferred embodiment, stage i) and/or stage ii) are carried out in the presence of hydrofluoric acid having an electrical conductivity of less than 10 mS/cm.

DETAILED DESCRIPTION OF THE PRESENT INVENTION

The present invention relates to a process for the production of 2,3,3,3-tetrafluoropropene comprising the stages:

i) in a first reactor, bringing a stream A comprising 2-chloro-3,3,3-trifluoropropene into contact with hydrofluoric acid in the gas phase in the presence of a catalyst in order to produce a stream B comprising 2,3,3,3-tetrafluoropropene, HCl, HF and unreacted 2-chloro-3,3,3-trifluoropropene; and ii) in a second reactor, bringing hydrofluoric acid into contact, in the gas phase in the presence or not of a catalyst, with a stream comprising at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream C comprising 2-chloro-3,3,3-trifluoropropene.

Preferably, the stream B obtained in stage i) feeds said second reactor used for stage ii).

According to a preferred embodiment, the electrical conductivity of said stream A provided in stage i) is less than 15 mS/cm. Advantageously, the electrical conductivity of said stream A provided in stage i) is less than 14 mS/cm, preferably less than 13 mS/cm, more preferentially less than 12 mS/cm, in particular less than 11 mS/cm, more particularly less than 10 mS/cm, favorably less than 9 mS/cm, advantageously favorably less than 8 mS/cm, preferentially favorably less than 7 mS/cm, more preferentially favorably less than 6 mS/cm, particularly favorably less than 5 mS/cm. The electrical conductivity is measured using an inductive conductivity measurement cell and according to the practice known to a person skilled in the art. The electrical conductivity is measured at ambient temperature. The electrical conductivity is measured at a pressure equal to the pressure at which stage b) is carried out. The electrical conductivity of the stream A can be reduced, in order to achieve a conductivity of less than 15 mS/cm, by reducing the concentration of electrolyte possibly present in the latter according to techniques known to a person skilled in the art (distillation, cooling and separation by settling, passing through 3 to 5 A molecular sieves or zeolites). Preferably, the measurement cell is coated with a material resistant to a corrosive medium, in particular resistant to hydrofluoric acid.

The electrical conductivity of said stream A is measured prior to stage i). Preferably, the electrical conductivity of said stream A is measured when the latter is in the liquid form. Said process according to the present invention can thus comprise a stage of heating and vaporization of said stream A prior to the implementation of stage i) in order to provide said stream A in the gaseous form. Preferably, said stream A employed in stage i) is in the gaseous form as it is brought into contact with HF.

Preferably, stage i) is carried out in the presence of a catalyst. Preferably, stage ii) is carried out in the presence or in the absence of a catalyst; in particular, stage ii) is carried out in the presence of a catalyst. Preferably, the catalyst is chromium-based. Preferably, the chromium-based catalyst can be a chromium oxide (for example $CrO_2$, $CrO_3$ or $Cr_2O_3$), a chromium oxyfluoride or a chromium fluoride (for example $CrF_3$) or a mixture of these. The chromium oxyfluoride can contain a fluorine content of between 1% and 60% by weight, based on the total weight of the chromium oxyfluoride, advantageously between 5% and 55% by weight, preferably between 10% and 52% by weight, more preferentially between 15% and 52% by weight, in particular between 20% and 50% by weight, more particularly between 25% and 45% by weight, favorably between 30% and 45% by weight, more favorably from 35% to 45% by weight, of fluorine, based on the total weight of the chromium oxyfluoride. The catalyst can also comprise a cocatalyst chosen from the group consisting of Ni, Co, Zn, Mg, Mn, Fe, Zn, Ti, V, Zr, Mo, Ge, Sn, Pb and Sb; preferably Ni, Co, Zn, Mg and Mn; in particular Ni, Co and Zn. The content by weight of the cocatalyst is between 1% and 10% by weight, based on the total weight of the catalyst. The catalyst may or may not be supported. A support, such as alumina, activated alumina, aluminum halides ($AlF_3$, for example), aluminum oxyhalides, activated carbon, magnesium fluoride or graphite, can be used.

Preferably, the catalyst can have a specific surface between 70 and 225 $m^2/g$, advantageously between 90 and 200 $m^2/g$, preferably between 100 and 190 $m^2/g$, in particular between 125 and 180 $m^2/g$. Alternatively, the catalyst can have a specific surface between 1 and 100 $m^2/g$, preferably between 5 and 80 $m^2/g$, more preferentially between 5 and 70 $m^2/g$, ideally between 5 and 50 $m^2/g$, in particular between 10 and 50 $m^2/g$, more particularly between 15 and 45 $m^2/g$.

According to a preferred embodiment, the electrical conductivity of said stream comprising at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene is less than 15 mS/cm. Advantageously, the electrical conductivity of said stream comprising at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene is less than 14 mS/cm, preferably less than 13 mS/cm, more preferentially less than 12 mS/cm, in particular less than 11 mS/cm, more particularly less than 10 mS/cm, favorably less than 9 mS/cm, advantageously favorably less than 8 mS/cm, preferentially favorably less than 7 mS/cm, more preferentially favorably less than 6 mS/cm, particularly favorably less than 5 mS/cm.

According to a specific embodiment, the hydrofluoric acid used in stage ii) results from the stream B of stage i). Hydrofluoric acid can also be added to the stream B before, or at the same time as, it is brought into contact with said stream comprising at least one chlorinated compound as defined in the present invention.

According to a preferred embodiment, said stream B, to which hydrofluoric acid is optionally added, and said at least one chlorinated compound are brought into contact prior to the entry of these into said second reactor. Preferably, said at least one chlorinated compound is in the liquid state. The latter is vaporized by mixing with said stream B, to which hydrofluoric acid is optionally added. The resulting mixture is then in the gaseous form. In particular, the mixing between said stream B, to which hydrofluoric acid is optionally added, and said at least one chlorinated compound is carried out in a static mixer. Preferably, said at least one chlorinated compound is introduced into the static mixer via one or more spray nozzles. Said at least one chlorinated compound is thus sprayed in the form of droplets before being vaporized by mixing with said stream B, to which hydrofluoric acid is optionally added, thus forming a mixture in the gaseous form. The spraying of said at least one chlorinated compound in the form of fine droplets makes it possible to ensure a more efficient vaporization of this compound. For example, the mean diameter of the droplets thus produced can be less than 500 μm.

According to a preferred embodiment, the pressure at the inlet of said first reactor is atmospheric pressure or a pressure greater than that; advantageously, the pressure at the inlet of said first reactor is greater than 1.5 bara, preferably greater than 2.0 bara, in particular greater than 2.5 bara, more particularly greater than 3.0 bara. Preferably, stage i) is carried out at a pressure at the inlet of said first reactor of between atmospheric pressure and 20 bara, preferably between 2 and 18 bara, more preferentially between 3 and 15 bara.

Preferably, stage i) of the present process is carried out with a contact time between 1 and 100 s, preferably between 2 and 75 s, in particular between 3 and 50 s. Preferably, the HF/1233xf molar ratio can vary between 1:1 and 150:1, preferably between 2:1 and 125:1, more preferentially between 3:1 and 100:1. An oxidant, such as oxygen or chlorine, can be added during stage i). The molar ratio of the oxidant to the hydrocarbon compound can be between 0.005 and 2, preferably between 0.01 and 1.5. The oxidant can be pure oxygen, air or a mixture of oxygen and nitrogen.

According to a preferred embodiment, the pressure at the inlet of said first reactor of stage i) is greater than the pressure at the inlet of said second reactor of stage ii); preferably, the pressure difference between the pressure at the inlet of said first reactor and the pressure at the inlet of said second reactor is from 100 mbar to 3.5 bar, advantageously from 150 mbar to 3.0 bar, preferably from 300 mbar to 2.5 bar, more preferentially from 400 mbar to 2.0 bar, in particular from 750 mbar to 1.75 bar, more particularly from 1 to 1.5 bar.

As mentioned above, the pressure at the inlet of said second reactor is less than that at the inlet of said first reactor. Thus, the pressure at the inlet of said second reactor can be less than atmospheric pressure. The pressure at the inlet of said second reactor can be greater than 1.5 bara while being less than that at the inlet of said first reactor, preferably greater than 2.0 bara while being less than that at the inlet of said first reactor, in particular greater than 2.5 bara while being less than that at the inlet of said first reactor, more particularly greater than 3.0 bara while being less than that at the inlet of said first reactor. Preferably, stage ii) is carried out at a pressure between atmospheric pressure and 20 bara while being less than that at the inlet of said first reactor, preferably between 2 and 18 bara while being less than that at the inlet of said first reactor, more preferentially between 3 and 15 bara while being less than that at the inlet of said first reactor.

Preferably, stage ii) of the present process is carried out with a contact time between 1 and 100 s, preferably between 2 and 75 s, in particular between 3 and 50 s. Preferably, the HF/chlorinated compound molar ratio can vary between 1:1 and 150:1, preferably between 2:1 and 125:1, more preferentially between 3:1 and 100:1. An oxidant, such as oxygen or chlorine, can be added during stage ii). The molar ratio of the oxidant to the hydrocarbon compound can be between 0.005 and 2, preferably between 0.01 and 1.5. The oxidant can be pure oxygen, air or a mixture of oxygen and nitrogen.

According to a preferred embodiment, stage i) is carried out at a temperature of between 310° C. and 420° C., advantageously between 310° C. and 400° C., preferably between 310° C. and 375° C., more preferentially between 310° C. and 360° C., in particular between 330° C. and 360° C.

According to a preferred embodiment, stage ii) is carried out at a temperature of between 320° C. and 440° C., advantageously between 320° C. and 420° C., preferably between 330° C. and 400° C., more preferentially between 330° C. and 390° C., in particular between 340° C. and 380° C.

Stage i) can be carried out at a temperature different from or equal to that of stage ii). When stage i) is carried out at a temperature different from that of stage ii), stage i) can be carried out at a temperature lower than that of stage ii) or at a temperature greater than that of stage ii).

According to a preferred embodiment, the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C.; and less than 60° C., advantageously less than 55° C., preferably less than 50° C., more preferentially less than 45° C., in particular less than 40° C., more particularly less than 35° C., favorably less than 30° C., preferentially favorably less than 25° C., particularly favorably less than 20° C.

Preferably, stage i) is carried out at a temperature which is lower than the temperature at which stage ii) is carried out; and the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C.

Preferably, stage i) is carried out at a temperature which is lower than the temperature at which stage ii) is carried out; and the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C., and less than 60° C., advantageously less than 55° C., preferably less than 50° C., more preferentially less than 45° C., in particular less than 40° C., more particularly less than 35° C., favorably less than 30° C., preferentially favorably less than 25° C., particularly favorably less than 20° C.

Alternatively, stage i) is carried out at a temperature which is greater than the temperature at which stage ii) is carried out; and the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C.

Preferably, stage i) is carried out at a temperature which is greater than the temperature at which stage ii) is carried out; and the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C., and less than 60° C., advantageously less than 55° C., preferably less than 50° C., more preferentially less than 45° C., in particular less than 40° C., more particularly less than 35° C., favorably less than 30° C., preferentially favorably less than 25° C., particularly favorably less than 20° C.

Preferably, besides 2-chloro-3,3,3-trifluoropropene, the stream C also comprises 2,3,3,3-tetrafluoropropene, HF, HCl and 1,1,1,2,2-pentafluoropropane. The stream C can be purified, preferably by distillation, in order to form a stream C1 comprising 2,3,3,3-tetrafluoropropene, HCl and 1,1,1,2,2-pentafluoropropane and a stream C2 comprising HF and 2-chloro-3,3,3-trifluoropropene.

Preferably, said stream C is distilled under conditions sufficient to form said stream C1 comprising 2,3,3,3-tetrafluoropropene, HCl and 1,1,1,2,2-pentafluoropropane, and said stream C2 comprising HF and 2-chloro-3,3,3-trifluoropropene. In particular, the distillation can be carried out at a pressure of 2 to 6 bara, more particularly at a pressure of 3 to 5 bara. In particular, the temperature at the distillation column top is from −35° C. to 10° C., preferably from −20° C. to 0° C.

Preferably, said stream C2 is recycled in stage i). Said stream C2 can optionally be purified, in particular by distillation, before being recycled in stage i). The purification of said second stream can optionally be carried out for impurities possibly present in the latter. Said stream C2 recycled in stage i) can have an electrical conductivity of less than 15 mS/cm.

According to a preferred embodiment, said stream C obtained in stage ii) is cooled prior to the abovementioned purification. In particular, said stream C obtained in stage ii) is cooled to a temperature of less than 100° C., then distilled in order to form said first stream comprising 2,3,3,3-tetrafluoropropene, HCl and 1,1,1,2,2-pentafluoropropane and said second stream comprising HF and 2-chloro-3,3,3-trifluoropropene; the temperature at the distillation column top is from −35° C. to 10° C. and the distillation is carried out at a pressure from 2 to 6 bara; said second stream obtained at the distillation column bottom is recycled in stage i).

Said stream C can be cooled, before distillation, to a temperature of less than 95° C., advantageously of less than 90° C., preferably of less than 85° C., more preferentially of less than 80° C., in particular of less than 70° C., more particularly of less than 60° C., favorably of less than 55° C., advantageously favorably of less than 50° C., preferentially favorably of less than 40° C., more preferentially favorably of less than 30° C., particularly favorably of less than 25° C., more particularly favorably of less than 20° C. The cooling of the flow of products obtained to such temperatures facilitates the subsequent distillation.

The cooling of said stream C can be carried out by virtue of one or a plurality of heat exchangers. The cooling of said stream C can be carried out by passing the latter through one, two, three, four, five, six, seven, eight, nine or ten heat exchangers; preferably, the number of heat exchangers is between 2 and 8, in particular between 3 and 7.

According to a preferred embodiment, stage i) and stage ii) are carried out in the presence of hydrofluoric acid having an electrical conductivity of less than 10 mS/cm, preferably of less than 5 mS/cm. The electrical conductivity of the hydrofluoric acid can be measured prior to its use in stage i) and/or in stage ii) of the present process. Preferably, the electrical conductivity of the hydrofluoric acid is measured prior to stage i) and/or to stage ii) and the hydrofluoric acid is in the liquid form during the measurement. The process can also comprise a stage of heating and of vaporization of the hydrofluoric acid prior to the implementation to stage i) and/or to stage ii) in order to provide hydrofluoric acid in the gaseous form. Preferably, the hydrofluoric acid is in the gaseous form as it is brought into contact with said stream A or with said at least one chlorinated compound.

Preferably, the process according to the present invention is carried out continuously.

EXAMPLE

The fluorination of HCFO-1233xf (2-chloro-3,3,3-trifluoropropene) to give HFO-1234yf (2,3,3,3-tetrafluoropropene) and optionally to give HFC-245cb (1,1,1,2,2-pentafluoropropane) is carried out in a first multitubular reactor. The stream of products which results from this fluorination feeds a second reactor. Said second reactor is also fed with a flow of hydrofluoric acid and of 1,1,1,2,3-pentachloropropane (HCC-240db). The fluorination of HCC-240db to give HCFO-1233xf (2-chloro-3,3,3-trifluoropropene) is carried out in the second multitubular reactor. A recycling loop, the flow rate of which is controlled, makes it possible to return certain products to the first reactor. The first and the second reactor contain a bulk catalyst based on chromium oxide. The catalyst is activated by a series of stages comprising drying, fluorination, treatment under air and fluorination with recycling. This multistage treatment makes it possible to render the catalytic solid active and selective. The flow exiting from said second reactor is treated by distillation in order to form a stream comprising HFO-1234yf and HCl possibly HFC-245cb and a stream comprising HF and HCFO-1233xf. The latter stream comprising HF and HCFO-1233xf constitutes the stream resulting from the recycling loop (stream C2).

In the first reactor, the fluorination process is carried out following the following operating conditions:
  an absolute pressure in the fluorination reactor of 6.1 bar absolute
  a molar ratio of the HF to the sum of the organic materials fed by the recycling loop of between 15 and 20 (i.e., the sum of the organic materials contained in the stream resulting from the recycling loop or stream C2)
  a contact time of between 18 and 20 seconds
  a constant temperature in the reactor of 330° C.

In the second reactor, the fluorination process is carried out following the following operating conditions:
  an absolute pressure in the fluorination reactor of 5.5 bar absolute
  a molar ratio of the HF to the sum of the organic materials fed by the recycling loop of between 12 and 15
  a contact time of between 11 and 13 seconds
  a constant temperature in the reactor of 340° C.

The process is carried out with a stream of HCFO-1233xf having two different electrical conductivity values: 6 and 20 mS/cm. The electrical conductivity was measured at ambient temperature and at 5.5 bara. The run is halted when the conversion of 2-chloro-3,3,3-trifluoropropene is less than 50% in the first reactor. The values obtained are taken up in table 1 below. The electrical conductivity of the stream of HCFO-1233xf is measured using a cell sold by Endress+Hauser and referenced under the term InduMax P CLS 50 coated with a polymer coating of perfluoroalkoxy (PFA) type resistant to a corrosive medium containing HF.

TABLE 1

| Example | Electrical conductivity (mS/cm) | Duration of the run to achieve a conversion <50% (h) |
|---|---|---|
| 1 (inv.) | 6 | 410 |
| 2 (comp.) | 20 | 150 |

The results given in detail in table 1 demonstrate that a stream comprising HCFO-1233xf and having an electrical conductivity of less than 15 mS/cm makes it possible to maintain a sufficiently high conversion for a significant period of time. This is because a conversion of greater than 50% can be maintained for up to 400 h when the electrical conductivity is 6 mS/cm (example 1). On the contrary, the conversion of HCFO-1233xf falls strongly when the electrical conductivity is too high (example 2).

The invention claimed is:

1. A process for the production of 2,3,3,3-tetrafluoropropene comprising the stages:
   i) in a first reactor, bringing a stream A comprising 2-chloro-3,3,3-trifluoropropene into contact with hydrofluoric acid in the gas phase in the presence of a catalyst in order to produce a stream B comprising 2,3,3,3-tetrafluoropropene, HCl, HF and unreacted 2-chloro-3,3,3-trifluoropropene; and
   ii) in a second reactor, bringing hydrofluoric acid into contact, in the gas phase in the presence or not of a catalyst, with at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream C comprising 2-chloro-3,3,3-trifluoropropene,
   wherein the stream B obtained in stage i) feeds said second reactor used for stage ii); and wherein an electrical conductivity of said stream A provided in stage i) is less than 15 mS/cm.

2. The process as claimed in claim 1, wherein stage i) is carried out in the presence of a catalyst; and stage ii) is carried out in the presence or in the absence of a catalyst.

3. The process as claimed in claim 2, wherein the catalyst is based on chromium and also comprises a cocatalyst selected from the group consisting of Ni, Zn, Co, Mn and Mg.

4. The process as claimed in claim 1, wherein the stream C also comprises 2,3,3,3-tetrafluoropropene, HF, HCl and 1,1,1,2,2-pentafluoropropane.

5. The process as claimed in claim 1, wherein the stream C is purified in order to form a stream C1 comprising 2,3,3,3-tetrafluoropropene, HCl and 1,1,1,2,2-pentafluoropropane, and a stream C2 comprising HF and 2-chloro-3,3,3-trifluoropropene.

6. The process as claimed in claim 1, wherein said stream C2 is recycled in stage i).

7. The process as claimed in claim 6, wherein said stream C2 recycled in stage i) has an electrical conductivity of less than 15 mS/cm.

8. The process as claimed in claim 1, wherein said stream B and said at least one chlorinated compound are brought into contact prior to the entry of these into said second reactor.

9. The process as claimed in claim 1, wherein the pressure at the inlet of said first reactor of stage i) is greater than the pressure at the inlet of said second reactor of stage ii).

10. The process as claimed in claim 1, wherein the temperature at which stage i) is carried out is different from that at which stage ii) is carried out; and the difference between the temperature at which stage i) is carried out and the temperature at which stage ii) is carried out is greater than 0.2° C.

11. The process as claimed in claim 10, wherein stage i) is carried out at a temperature which is lower than the temperature at which stage ii) is carried out; and the difference between the temperature at which stage i) is carried out and the temperature at which stage ii) is carried out is greater than 0.2° C.

12. The process as claimed in claim 1, wherein the stream C is cooled to a temperature of less than 100° C., then distilled in order to form a stream C1 comprising 2,3,3,3-tetrafluoropropene, HCl and 1,1,1,2,2-pentafluoropropane, and a stream C2 comprising HF and 2-chloro-3,3,3-trifluoropropene; the temperature at the distillation column top is from −35° C. to 10° C. and the distillation is carried out at a pressure from 2 to 6 bara; said second stream obtained at the distillation column bottom is recycled in stage i).

13. The process as claimed in claim 1, wherein stage i) and/or stage ii) are carried out in the presence of hydrofluoric acid having an electrical conductivity of less than 10 mS/cm.

* * * * *